(12) United States Patent
Watanabe et al.

(10) Patent No.: US 7,807,600 B2
(45) Date of Patent: Oct. 5, 2010

(54) CATALYST FOR ACRYLONITRILE SYNTHESIS

(75) Inventors: Seigo Watanabe, Iwakuni (JP); Koichi Mizutani, Yokohama (JP); Motoo Yanagita, Yokohama (JP); Jinko Izumi, Toyohashi (JP)

(73) Assignee: Dia-Nitrix Co., Ltd., Tokyo (JP)

( * ) Notice: Subject to any disclaimer, the term of this patent is extended or adjusted under 35 U.S.C. 154(b) by 0 days.

(21) Appl. No.: 10/553,200

(22) PCT Filed: Apr. 14, 2004

(86) PCT No.: PCT/JP2004/005332

§ 371 (c)(1),
(2), (4) Date: Oct. 13, 2005

(87) PCT Pub. No.: WO2004/091776

PCT Pub. Date: Oct. 28, 2004

(65) Prior Publication Data

US 2006/0194693 A1    Aug. 31, 2006

(30) Foreign Application Priority Data

Apr. 18, 2003   (JP) .............................. 2003-114131

(51) Int. Cl.
  *B01J 23/00*  (2006.01)
  *B01J 21/00*  (2006.01)
  *B01J 20/00*  (2006.01)

(52) U.S. Cl. ...................... 502/255; 502/305; 502/311; 502/312; 502/313; 502/314; 502/315; 502/316; 502/317; 502/318; 502/321

(58) Field of Classification Search ................. 502/305, 502/311, 316, 321, 322, 248, 249, 255, 258
See application file for complete search history.

(56) References Cited

U.S. PATENT DOCUMENTS

| 3,879,453 | A | * | 4/1975 | Ono et al. ................... 562/547 |
| 4,009,194 | A | * | 2/1977 | Umemura et al. ........... 558/324 |
| 4,087,382 | A | * | 5/1978 | Khoobiar .................... 502/249 |
| RE30,545 | E | * | 3/1981 | Khoobiar .................... 502/249 |
| 4,316,856 | A | * | 2/1982 | Guttmann et al. ........... 558/322 |
| 4,443,556 | A | * | 4/1984 | Aoki et al. .................. 502/212 |
| 4,774,352 | A | * | 9/1988 | Sasaki et al. ................ 558/322 |
| 4,843,055 | A | * | 6/1989 | Glaeser et al. .............. 502/202 |
| 4,978,765 | A | * | 12/1990 | Sasaki et al. ................ 558/324 |
| 5,059,573 | A | * | 10/1991 | Sasaki et al. ................ 502/205 |
| 5,094,990 | A | * | 3/1992 | Sasaki et al. ................ 502/214 |
| 5,132,269 | A | * | 7/1992 | Sasaki et al. ................ 502/205 |
| 5,688,739 | A | | 11/1997 | Drenski et al. |
| 5,780,664 | A | * | 7/1998 | Aoki .......................... 558/323 |
| 5,877,381 | A | * | 3/1999 | Sasaki et al. ................ 585/658 |
| 6,017,846 | A | * | 1/2000 | Abdulwahed et al. ....... 502/300 |
| 6,037,304 | A | * | 3/2000 | Abdulwahed et al. ....... 502/300 |
| 6,124,233 | A | * | 9/2000 | Abdulwahed et al. ....... 502/312 |
| 6,479,691 | B1 | * | 11/2002 | Sasaki et al. ................ 558/321 |
| 6,486,091 | B1 | * | 11/2002 | Abdulwahed et al. ....... 502/312 |
| 6,559,085 | B1 | * | 5/2003 | Sasaki et al. ................. 502/22 |
| 6,596,897 | B1 | * | 7/2003 | Guan et al. .................. 558/323 |
| 6,642,405 | B1 | * | 11/2003 | Mori et al. ................... 558/338 |
| 6,653,496 | B1 | * | 11/2003 | Mori et al. ................... 558/308 |
| 6,700,769 | B2 | * | 3/2004 | Phillips et al. .............. 361/119 |
| 6,878,847 | B2 | * | 4/2005 | Kasuga et al. ............... 562/532 |
| 6,881,702 | B2 | * | 4/2005 | Arnold et al. ............... 502/311 |
| 6,924,387 | B1 | * | 8/2005 | Chang et al. ................ 558/323 |
| 6,946,422 | B2 | * | 9/2005 | Stevenson et al. ........... 502/311 |
| 7,365,041 | B2 | | 4/2008 | Miyaki et al. |

FOREIGN PATENT DOCUMENTS

| JP | 59-204163 | 11/1984 |
| JP | 61-13701 | 4/1986 |
| JP | 63-295546 | 12/1988 |
| JP | 01-228950 | 9/1989 |
| JP | 3-217794 | 9/1991 |
| JP | 3217794 | 9/1991 |
| JP | 10-043595 | 2/1998 |
| JP | 10-156185 | 6/1998 |
| JP | 2000-070714 | 3/2000 |
| JP | 2000-126599 | 5/2000 |
| JP | 2003-64042 | 3/2003 |
| JP | 2003-64043 | 3/2003 |
| JP | 2003-71283 | 3/2003 |

OTHER PUBLICATIONS

U.S. Appl. No. 12/446,759, filed Apr. 23, 2009, Yanagita, et al.
U.S. Appl. No. 12/398,619, filed Mar. 5, 2009, Miyaki, et al.
U.S. Appl. No. 12/393,494, filed Feb. 26, 2009, Watanabe, et al.

\* cited by examiner

*Primary Examiner*—Cam N Nguyen
(74) *Attorney, Agent, or Firm*—Oblon, Spivak, McClelland, Maier & Neustadt, L.L.P.

(57) ABSTRACT

A catalyst for acrylonitrile synthesis is disclosed which is composed of particles containing silica and a composite oxide including at least molybdenum. When the Mo/Si atomic ratio in bulk composition of the catalyst is represented by A and the Mo/Si atomic ratio in surface composition of the particles is represented by B, B/A is not more than 0.6.

6 Claims, No Drawings

CATALYST FOR ACRYLONITRILE SYNTHESIS

CROSS REFERENCE TO RELATED APPLICATION

This application is a 371 of PCT/JP04/005332, filed on Apr. 14, 2004, and claims priority to Japanese Patent Application No. JP 2003-114131, filed on Apr. 18, 2003.

TECHNICAL FIELD

The present invention relates to a catalyst used for synthesizing acrylonitrile by gas-phase catalytic ammoxidation of propylene with molecular oxygen and ammonia.

The present application claims the priority of Japanese Patent Application No. 2003-114131 filed on Apr. 18, 2003, the contents of which are incorporated herein by reference.

BACKGROUND ART

Well-known catalysts for acrylonitrile synthesis synthesize acrylonitrile from propylene in a fluid bed ammoxidation process and so forth, and many proposals have been made regarding such catalysts, which are presently used in industry worldwide.

For example, Japanese Patent Application, Second Publication No. S61-13701, Japanese Patent Application, First Publication No. S59-204163, Japanese Patent Application, First Publication No. H1-228950, Japanese Patent Application, First Publication No. H10-43595, Japanese Patent Application, First Publication No. H10-156185 and U.S. Pat. No. 5,688,739 (hereinafter, expressed as prior art document group 1) disclose a catalyst composed mainly of molybdenum and bismuth. Further, Japanese Patent No. 3217794 discloses a method to maintain acrylonitrile yield at a high level for a long time by keeping the atomic ratio of molybdenum to other metal components in the bulk composition of the catalyst within a certain range, in the case of producing acrylonitrile in a fluid bed using a catalyst containing molybdenum.

However, prior art document group 1 intended mainly to improve so-called catalyst initial characteristics such as activity, selectivity, etc. by specifying catalyst component elements and their bulk compositional ratios and there was no reference to catalyst structural design technology to maintain catalytic activity and selectivity at a high level for a long time. On the other hand, Japanese Patent No. 3217794 discloses a method to maintain acrylonitrile yield at a high level for a long time, however, performing the disclosed method alone is insufficient to attain this goal and further improvement is necessary from the industrial point of view.

DISCLOSURE OF INVENTION

The present invention has been achieved taking into consideration the above-mentioned circumstances and an object is to provide a catalyst for acrylonitrile synthesis which is able to maintain the acrylonitrile yield at a high level for a long time when propylene is subjected to gas phase catalytic ammoxidation.

The present inventors have found that to maintain the acrylonitrile yield at a high level for a long time when using a particulate catalyst containing silica and a composite oxide including at least molybdenum and continuing the reaction for a long time, for example, in a fluid bed reactor, it is important to control the ratio of the Mo/Si atomic ratio in surface composition of the catalyst particles to the Mo/Si atomic ratio in bulk composition of the catalyst to become not greater than a certain value, and thus the present invention has been completed.

In other words, a catalyst for acrylonitrile synthesis in the present invention is characterized to be a catalyst comprising a particle containing silica and a composite oxide including at least molybdenum wherein the Mo/Si atomic ratio in bulk composition of the catalyst, expressed as A, and the Mo/Si atomic ratio in surface composition of the catalyst particles, expressed as B, have a relationship such that B/A is not greater than 0.6.

Using this catalyst in a reaction for synthesizing acrylonitrile by gas-phase catalytic ammoxidation of propylene with molecular oxygen and ammonia, the acrylonitrile yield, especially, acrylonitrile selectivity can be maintained at a high level for a long time.

BEST MODE FOR CARRYING OUT THE INVENTION

The present invention is described below in more detail.

A catalyst for acrylonitrile synthesis in the present invention is a catalyst comprising a particle containing silica and a composite oxide including at least molybdenum, and is used when synthesizing acrylonitrile by gas-phase catalytic ammoxidation of propylene with molecular oxygen and ammonia, and further, the Mo/Si atomic ratio in bulk composition of the catalyst, expressed as A, and the Mo/Si atomic ratio in surface composition of the catalyst particles, expressed as B, have a relationship such that B/A is not greater than 0.6.

"The catalyst bulk composition" here denotes a composition of the whole aggregate of the catalyst particulates of at least several tens of milligrams. Although there are not any special restrictions in the methods of measuring the Mo/Si atomic ratio in bulk composition of the catalyst, the following method, for example, is preferable wherein more than 50 mg of the catalyst is dissolved in a mixed solution of hydrofluoric acid, hydrochloric acid and hydroiodic acid and quantitative analysis of Mo and Si in this solution is performed with ICP emission spectrometry and the Mo/Si atomic ratio is obtained. Usually, the Mo/Si atomic ratio in bulk composition of the catalyst is thought to be equal to this ratio of the charged raw materials in the preparation stage of the catalyst.

On the other hand, the catalyst particle surface composition denotes the ratio of elements composing the very surface layer of each catalyst particle. The very surface layer above denotes the layer from the particle surface to a depth of around several nanometers and "the Mo/Si atomic ratio in surface composition of the catalyst particles" is defined as the Mo/Si atomic ratio calculated using X-ray Photoelectron Spectroscopy (XPS), measuring XPS spectra of the catalyst with the X-ray source of an Al-k$\alpha$ line, calculating peak area intensities of Mo3d and Si2p, correcting the peak area intensities thus obtained with relative sensitivity factors inherent to the apparatus and using these values for the basis of the calculation.

A catalyst which has a lower B/A value shows lesser decrease with time in acrylonitrile yield, especially, a lesser decrease in acrylonitrile selectivity, when performing gas-phase ammoxidation of propylene, and in particular when using a catalyst with a B/A value of not greater than 0.6, an even lesser decrease with time in acrylonitrile yield, especially, an even lesser decrease in acrylonitrile selectivity is realized and acrylonitrile yield can be maintained at a high level for a long time. The B/A value is preferably not greater than 0.45 and more preferably not greater than 0.3.

The method for preparing the catalyst for acrylonitrile synthesis is not particularly limited as long as it can produce a catalyst comprising a particle containing silica and a composite oxide including at least molybdenum and having a B/A value of not greater than 0.6, however, a specific method is particularly preferable that has a process for preparing an aqueous slurry containing molybdenum and silica, a process for drying this aqueous slurry and a process for calcining this dried material.

The method for preparing the aqueous slurry may be performed by adding at least a raw material of molybdenum and silica to water and stirring them.

The liquid temperature when preparing the aqueous slurry is not particularly limited, however, it is preferable that it be not greater than 60° C., and more preferable to be not greater than 45° C. When the liquid temperature exceeds 60° C., it may be difficult to obtain a catalyst having a B/A value of not greater than 0.6.

It is possible, if necessary, to give heat treatment to the resultant slurry such as aging, concentration etc. within the temperature range from 70° C. to 105° C., however, it is preferable not to give such heat treatment in order to obtain a catalyst having a B/A value of not greater than 0.6.

The raw material of molybdenum used in preparing the aqueous slurry is not particularly limited and ammonium paramolybdate, ammonium dimolybdate, molybdenum trioxide, molybdenum dioxide, molybdic acid, molybdenum chloride etc can be used.

Further, depending on the raw materials used other than molybdenum and silica, it is possible to add to the aqueous slurry a component which adjusts the solubility of these materials in water, and in the case of using nitrate as a raw material, for example, nitric acid may be used in such an amount that it reaches a concentration of 0.1 to 4 wt % in the aqueous slurry.

As for a raw material of silica, it is preferable to use colloidal silica (silica gel) and those sold on the market can be appropriately selected. Further, a size (diameter) of the colloidal particle is not particularly limited, however, it is preferable to be 2 to 100 nm, and more preferable to be 5 to 50 nm. Also, a size of the colloidal particle can be either homogeneous or a mixture of several sizes.

The amount of water used in the aqueous slurry is preferably chosen so as to make the solid content of the slurry become 10 to 40 wt %, and more preferably, become 15 to 30 wt %.

Moreover, the aqueous slurry may contain other components in addition to molybdenum and silica.

Specifically, a more preferable bulk composition of the catalyst for acrylonitrile synthesis finally obtained is a composition expressed by the following formula 1 or formula 2 and it is preferable to previously add to the aqueous slurry raw materials of the elements shown as C, D, E in formula 1 and Sb (for example, nitrates, carbonates, acetates, ammonium salts, oxides, halides of these elements) or raw materials of the elements shown as F, G in formula 2 and Bi and Fe (for example, nitrates, carbonates, acetates, ammonium salts, oxides, halides of these elements) in order to realize such a bulk composition.

$$Sb_aMo_bC_cD_dE_eO_f(SiO_2)_g \qquad \text{FORMULA 1}$$

wherein, Sb, Mo and O represent antimony, molybdenum and oxygen, respectively; C represents at least one element selected from the group consisting of iron, cobalt, nickel, manganese, uranium, cerium, tin and copper; D represents at least one element selected from the group consisting of vanadium and tungsten; E represents at least one element selected from the group consisting of magnesium, calcium, strontium, barium, lanthanum, titanium, zirconium, niobium, tantalum, chromium, rhenium, ruthenium, osmium, rhodium, iridium, palladium, platinum, silver, zinc, cadmium, boron, aluminum, gallium, indium, sodium, potassium, rubidium, cesium, thallium, germanium, lead, phosphorus, arsenic, bismuth, selenium and tellurium; $SiO_2$ represents silica; subscripts a, b, c, d, e, f and g each represents an atomic ratio of each element; when a is 10, b is in a range of 0.1 to 15, c is in a range of 1 to 20, d is in a range of 0 to 10, e is in a range of 0 to 20, g is in a range of 10 to 200 and f represents the atomic ratio of oxygen that fulfills the requirement of the valence of each element above.

$$Mo_hBi_iFe_jF_kG_lO_m(SiO_2)_n \qquad \text{FORMULA 2}$$

wherein, Mo, Bi, Fe and O represent molybdenum, bismuth, iron and oxygen, respectively; F represents at least one element selected from the group consisting of sodium, potassium, rubidium, cesium and thallium; G represents at least one element selected from the group consisting of cobalt, nickel, copper, zinc, magnesium, calcium, strontium, barium, titanium, vanadium, chromium, manganese, tungsten, silver, aluminum, phosphorus, boron, tin, lead, gallium, germanium, arsenic, antimony, niobium, tantalum, zirconium, indium, sulfur, selenium, tellurium, lanthanum, cerium, praseodymium, neodymium, samarium, europium, gadolinium, terbium, holmium, erbium, thulium and ytterbium; $SiO_2$ represents silica; subscripts h, i, j, k, l, m and n each represents an atomic ratio of each element; when h is 12, i is in a range of 0.1 to 5, j is in a range of 0.1 to 10, k is in a range of 0.01 to 3, l is in a range of 0 to 20, n is in a range of 10 to 200 and m represents the atomic ratio of oxygen that fulfills the requirement of the valence of each element above.

Subsequently, the aqueous slurry thus obtained is dried. The drying method is not particularly limited, however, a spray dryer, particularly, a rotating disc type spray dryer, pressure nozzle type spray dryer and two-fluid nozzle type spray dryer is preferably used for the reason that the shape of the obtained dried material is desirable to be spherical and the adjustment of its particle size is relatively easy and, furthermore, the B/A value of the obtained catalyst is easily controlled to be not greater than 0.6. The external diameter of the dried material is desirable to be 1 to 200 μm and more desirable to be 5 to 150 μm.

On this occasion, it is preferable to control the temperature of the hot air flowing in a drying chamber of a spray dryer to a designated value, because this temperature is liable to affect the B/A value of the catalyst. Specifically, the temperature of the hot air flowing in a drying chamber is desirable to be 130 to 350° C. near the inlet of the drying chamber, and more desirable to be 140 to 300° C., and also, the temperature of the hot air near the outlet of the drying chamber is desirable to be 100 to 200° C., and more desirable to be 110 to 180° C. In addition, it is desirable to keep the difference between these temperatures near the inlet and near the outlet in the range of 20 to 60° C., and more desirable in the range of 25 to 45° C.

Then, the dried material thus obtained is further calcined to produce the catalyst for acrylonitrile synthesis.

The calcining temperature is not particularly limited, however, by calcining the dried material at a temperature in the range of 500 to 750° C., a favorable catalyst structure in terms of activity is formed and when using the catalyst thus obtained in ammoxidation of propylene, a high acrylonitrile yield can be maintained for a long time. In addition, it is preferable to carry out preliminary calcination at a low temperature before calcining at a temperature in the range of 500 to 750° C. The preliminary calcination may be performed at a temperature range, for example, of either around 250 to 400° C., or around 400 to 500° C., or both. When calcining at a temperature in the range of 500 to 750° C. after performing a preliminary calcination of one or two stages as above, a very favorable catalyst structure in terms of activity is formed and when using the catalyst thus obtained in ammoxidation of propylene, a high acrylonitrile yield can be maintained for a long time.

The calcining time is not particularly limited, however, it is preferable for it to take 1 hour or more. When the calcining time is less than 1 hour, sometimes, favorable catalyst structure for activity is not formed. More exactly, it is preferable to perform preliminary calcinations for 1 hour or more, and then to perform calcination at a temperature in the range of 500 to 750° C. for 1 hour or more.

The method of calcination is not particularly limited and a general purpose furnace can be used, however, a rotary kiln and a fluid bed calciner are particularly preferably used.

As for the atmosphere of calcination, air is particularly preferably used, but, inert gases such as nitrogen, carbon dioxide and so forth, nitrogen oxides, water vapor etc. may be contained as a portion.

The particle shape and size of the catalyst for acrylonitrile synthesis thus obtained are not particularly limited, however, a spherical form is particularly preferable for its shape and its external diameter is preferable to be 1 to 200 μm and more preferable to be 5 to 150 μm.

The method for synthesizing acrylonitrile through gas-phase catalytic ammoxidation of propylene with molecular oxygen and ammonia by using the catalyst thus obtained is not particularly limited, however, it is desirable to use a fluid bed reactor. After filling the catalyst into the fluid bed reactor, and introducing raw gases which contain at least molecular oxygen, ammonia and propylene and optionally diluted with inert gases and water vapor into the reactor, under the condition of, for example, 400 to 500° C. and ambient pressure to 300 kPa, propylene is catalytically ammoxidized to acrylonitrile in a gas phase.

The propylene concentration in the raw gases can be changed over a wide range and it is appropriate at 1 to 20 vol. %, and particularly desirable at 3 to 15 vol. %.

As an oxygen source of the raw gases, it is industrially beneficial to use air, but, it may be optional to add pure oxygen to it and use the oxygen-enriched air.

Further, the molar ratio of propylene to oxygen in the raw gases is desirable to be 1:1.5 to 1:3, and the molar ratio of propylene to ammonia is desirable to be 1:1 to 1:1.5.

As explained above, a catalyst for acrylonitrile synthesis comprising a particle containing silica and a composite oxide including at least molybdenum, and the Mo/Si atomic ratio in bulk composition of the catalyst, expressed as A, and the Mo/Si atomic ratio in surface composition of the catalyst particles, expressed as B, have a relationship such that B/A is not greater than 0.6, can maintain the acrylonitrile yield at a high level for a long time when performing gas phase catalytic ammoxidation of propylene.

The reason a catalyst can maintain the acrylonitrile yield at a high level for a long time when the Mo/Si atomic ratio in bulk composition of the catalyst (=A) and the Mo/Si atomic ratio in surface composition of the catalyst particles (=B) have a relationship such that B/A is not greater than a certain value as mentioned above is not clear, but, the fact that B/A is small means that silica is selectively concentrated near the particle surface of the catalyst particle structure and, at the same time, it means that there is less exposure of Mo at the particle surface. Therefore, it is possible that the loss of Mo component from the catalyst by sublimation and/or abrasion when used in a reaction is effectively reduced with the catalyst particle having such a structure.

In general, it is commonly accepted that it is desirable for a catalyst to have as homogeneous a distribution of its component elements within a particle structure as possible, but, it is particularly interesting that a catalyst which has selectively concentrated silica near the particle surface can maintain acrylonitrile yield at a high level for a long time, as mentioned above.

EXAMPLES

The present invention will be described in detail by way of examples and comparative examples. However, the present invention is not limited to these examples.

In the following examples and comparative examples, "part" means part by mass.

A test for catalytic activity and a quantitative analysis of the Mo/Si atomic ratio in bulk composition of the catalyst and the Mo/Si atomic ratio in surface composition of the catalyst particles were conducted as follows:

(1) Test for Catalytic Activity

Acrylonitrile was synthesized by ammoxidation of propylene utilizing a fluid bed reactor having an inner diameter of 2 inches.

A mixed gas having a composition of propylene/ammonia/air/water vapor=1/1.2/9.5/0.5 (molar ratio), as a raw gas, was introduced into the reactor at a linear velocity of the gaseous feedstock of 18 cm/sec. The reaction temperature and the reaction pressure were adjusted to 430° C. and 200 kPa, respectively.

The analysis of the product gas (reaction test analysis) was conducted by gas chromatography.

Contact time, conversion rate of propylene, selectivity to acrylonitrile and yield of acrylonitrile were defined as follows:

Contact time (sec)=volume of catalyst based on bulk density (L)/feed gas flow rate calculated in terms of reaction condition (L/sec)

Conversion rate of propylene (%)=Q/P×100

Selectivity to acrylonitrile (%)=R/Q×100

Yield of acrylonitrile (%)=R/P×100 wherein, P represents number of moles of fed propylene, Q represents number of moles of reacted propylene and R represents number of moles of produced acrylonitrile.

(2) Quantitative Analysis of the Mo/Si Atomic Ratio in Bulk Composition of the Catalyst To 0.5 g of a catalyst, 5 ml of 36 wt % hydrochloric acid, 10 ml of 57 wt % hydroiodic acid and 2.5 ml of 47 wt % hydrofluoric acid were successively added and the catalyst was completely dissolved under sealed conditions.

Subsequently, the resultant solution was transferred into a measuring flask made of polypropylene and diluted with water to a marked line to make a sample solution.

Then, the sample solution was suitably diluted and a quantitative analysis of Mo and Si in this solution was performed with ICP emission spectrometer (ICAP-577 manufactured by Japan Jarrel-Ash Co.) and the Mo/Si atomic ratio was obtained.

(3) Quantitative Analysis of the Mo/Si Atomic Ratio in Surface Composition of the Catalyst Particles The measurement was conducted by X-ray Photoelectron Spectrometer (ESCALAB220iXL manufactured by VG Co.) with the X-ray source of an Al-kα line.

From the XPS spectra obtained, first, by calculating peak area intensities of Mo3d and Si2p respectively, next, by correcting the peak area intensities with relative sensitivity factors inherent to the apparatus and then using these values for the basis of calculation, the Mo/Si atomic ratio in surface composition of the catalyst particles was obtained.

Example 1

To 1915 parts of 20 wt % colloidal silica (average colloid particle diameter of 20 nm), 3.3 parts of 85 wt % phosphoric acid was added. To this solution, 212.5 parts of ammonium paramolybdate dissolved in 640 parts of water was added while stirring and heated to 50° C. to make solution A.

Separately, 105.2 parts of bismuth nitrate was dissolved in 105 parts of 10 wt % nitric acid, and to this solution, 210.1 parts of nickel nitrate, 87.6 parts of iron (III) nitrate, 2.9 parts of potassium nitrate and 312 parts of water were added and heated to 50° C. to make solution B.

Further, separately, 930.5 parts of 61 wt % nitric acid and 843 parts of water were mixed, and to this solution, 104.7 parts of electrolytic iron powder was gradually added and dissolved. To this solution, 324.4 parts of antimony trioxide was added and heated at 100° C. for 2 hours. Subsequently, 10.2 parts of boric acid dissolved in 194 parts of water and 8.9 parts of 85 wt % phosphoric acid were added to this solution. After drying the resulting solution, the dried material was calcined at 950° C. for 3 hours, and then crushed. To 400 parts of the crushed material thus obtained, 600 parts of water was added and the mixture was ball-milled for 16 hours to make a liquid material. Then, the liquid material was heated to 50° C. to make solution C.

Solution A and solution B were mixed while stirring, then 831.1 parts of solution C was added and a slurry was obtained.

The resulting slurry was dried using a pressure nozzle type spray dryer in which the inlet temperature of hot air was controlled at 200° C. and the outlet temperature was controlled at 160° C. Approximately spherical particles were obtained as a dried material.

Subsequently, the resulting dried material was preliminarily calcined in air atmosphere at 250° C. for 2 hours and then at 400° C. for 2 hours, and finally calcined in a fluid bed calciner at 530° C. for 3 hours to obtain catalyst C1. The catalyst C1 was an approximately spherical particle with an average particle diameter of 57 μm.

The bulk composition of the catalyst C1 thus obtained was calculated from the amount of charged raw materials as shown in formula 3:

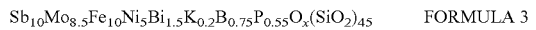
$$Sb_{10}Mo_{8.5}Fe_{10}Ni_5Bi_{1.5}K_{0.2}B_{0.75}P_{0.55}O_x(SiO_2)_{45} \quad \text{FORMULA 3}$$

wherein, x represents the atomic ratio of oxygen that fulfills the requirement of the valence of each element.

The Mo/Si atomic ratio in the bulk composition of the catalyst C1 measured with ICP emission spectrometry was 0.19. This value substantially coincided with the atomic ratio calculated from the amount of charged raw materials above, namely 8.5/45.

Further, the Mo/Si atomic ratio in surface composition of the particles of the catalyst C1 measured with X-ray Photoelectron Spectroscopy was 0.08.

That is, the ratio of the Mo/Si atomic ratio in surface composition of the catalyst particles to the Mo/Si atomic ratio in bulk composition of the catalyst in the catalyst C1 was 0.42.

The aforesaid activity test was performed with the catalyst C1 under the conditions that the contact time was 3.2 sec, and the conversion rate of propylene, selectivity to acrylonitrile and yield of acrylonitrile after 3 hours from the start of the reaction were 97.4%, 84.0% and 81.8%, respectively.

When the reaction was continued with the conditions left intact, and the analysis was performed again after 500 hours from the start of the reaction, the conversion rate of propylene, selectivity to acrylonitrile and yield of acrylonitrile were 97.2%, 83.4% and 81.1%, respectively.

Comparative Example 1

A slurry was obtained in the same manner as in Example 1, and the resulting slurry was dried using a pressure nozzle type spray dryer in which the inlet temperature of hot air was controlled at 330° C. and the outlet temperature was controlled at 190° C.

Subsequently, calcination was performed at 530° C. for 3 hours in a muffle furnace without a preliminary calcination to obtain catalyst C2.

The Mo/Si atomic ratio in the bulk composition of the catalyst C2 measured with ICP emission spectrometry was 0.19. This value was substantially the same as the one obtained with catalyst C1 in Example 1.

Further, the Mo/Si atomic ratio in surface composition of the particles of the catalyst C2 measured with X-ray Photoelectron Spectroscopy was 0.13.

That is, the ratio of the Mo/Si atomic ratio in surface composition of the catalyst particles to the Mo/Si atomic ratio in bulk composition of the catalyst in the catalyst C2 was 0.68.

The aforesaid activity test was performed with the catalyst C2 under the conditions that the contact time was 3.2 sec, and the conversion rate of propylene, selectivity to acrylonitrile and yield of acrylonitrile after 3 hours from the start of the reaction were 97.5%, 83.9% and 81.8%, respectively.

When the reaction was continued with the conditions left intact, and the analysis was performed again after 500 hours from the start of the reaction, the conversion rate of propylene, selectivity to acrylonitrile and yield of acrylonitrile were 96.9%, 82.4% and 79.8%, respectively.

Example 2

Ammonium paramolybdate (415.6 parts) was dissolved into a mixed solution of 1650.1 parts of 30 wt % colloidal silica (average colloid particle diameter of 25 nm) and 850 parts of water and heated to 40° C. to make solution D.

Separately, 142.6 parts of iron (III) nitrate, 285.1 parts of nickel nitrate, 57.1 parts of cobalt nitrate, 50.3 parts of magnesium nitrate, 46.8 parts of cerium nitrate, 42.8 parts of bismuth nitrate, 1.6 parts of potassium nitrate and 1.7 parts of rubidium nitrate were dissolved in 530 parts of 13 wt % nitric acid aqueous solution, and heated to 40° C. to make solution E.

While solution D was being thoroughly stirred, solution E was mixed into it and a slurry was obtained.

The resultant slurry was dried using a rotary disc type spray dryer in which the inlet temperature of hot air was controlled at 220° C. and the outlet temperature was controlled at 170° C. The dried material thus obtained was in the form of approximately spherical shaped particles.

Subsequently, the resulting dried material was preliminarily calcined at 300° C. for 2 hours and then at 450° C. for 2 hours, and finally calcined in fluid bed calciner at 590° C. for 3 hours to obtain catalyst C3. The catalyst C3 was approximately spherical particle with an average particle diameter of 58 μm.

The bulk composition of the catalyst C3 thus obtained was calculated from the amount of charged raw materials as shown in formula 4:

$$Mo_{12}Bi_{0.45}Fe_{1.8}Ni_5Co_1Mg_1Ce_{0.55}K_{0.08}Rb_{0.06}O_x(SiO_2)_{42} \quad \text{FORMULA 4}$$

wherein, x represents the atomic ratio of oxygen that fulfills the requirement of the valence of each element.

The Mo/Si atomic ratio in the bulk composition of the catalyst C3 measured with ICP emission spectrometry was 0.29. This value substantially coincided with the atomic ratio calculated from the amount of charged raw materials above, namely 12/42.

Further, the Mo/Si atomic ratio in surface composition of the particles of the catalyst C3 measured with X-ray Photoelectron Spectroscopy was 0.10.

That is, the ratio of the Mo/Si atomic ratio in surface composition of the catalyst particles to the Mo/Si atomic ratio in bulk composition of the catalyst in the catalyst C3 was 0.34.

The aforesaid activity test was performed with the catalyst C3 under the conditions that the contact time was 2.8 sec, and the conversion rate of propylene, selectivity to acrylonitrile and yield of acrylonitrile after 3 hours from the start of the reaction were 98.5%, 84.5% and 83.2% respectively.

When the reaction was continued with the conditions left intact, and the analysis was performed again after 500 hours from the start of the reaction, the conversion rate of propylene, selectivity to acrylonitrile and yield of acrylonitrile were 98.4%, 83.9% and 82.6%, respectively.

Example 3

A slurry was obtained in the same manner as in Example 2, and the resulting slurry was spray dried using a pressure nozzle type spray dryer in which the inlet temperature of hot air was controlled at 180° C. and the outlet temperature was controlled at 145° C. The dried material thus obtained was approximately spherical shaped particles.

Subsequently, catalyst C4 was obtained in the same manner as in Example 2. The catalyst C4 was in the form of approximately spherical shaped particles with an average particle diameter of 54 μm.

The Mo/Si atomic ratio in the bulk composition of the catalyst C4 measured with ICP emission spectrometry was 0.29. This value substantially coincided with the one obtained with the catalyst C3 in Example 2.

Further, the Mo/Si atomic ratio in surface composition of the particles of the catalyst C4 measured with X-ray Photoelectron Spectroscopy was 0.05.

That is, the ratio of the Mo/Si atomic ratio in surface composition of the catalyst particles to the Mo/Si atomic ratio in bulk composition of the catalyst in the catalyst C4 was 0.17.

The aforesaid activity test was performed with the catalyst C4 under the conditions that the contact time was 2.8 sec, and the conversion rate of propylene, selectivity to acrylonitrile and yield of acrylonitrile after 3 hours from the start of the reaction were 98.5%, 84.7% and 83.4%, respectively.

When the reaction was continued with the conditions left intact, and the analysis was performed again after 500 hours from the start of the reaction, the conversion rate of propylene, selectivity to acrylonitrile and yield of acrylonitrile were 98.4%, 84.3% and 83.0%, respectively.

Comparative Example 2

Solution D and solution E were prepared in the same manner as in Example 2, except that the temperature of both solutions was changed to 80° C.

While solution D was being thoroughly stirred, solution E was mixed into it and a slurry was obtained.

The resultant slurry was dried using a rotary disc type spray dryer in which the inlet temperature of hot air was controlled at 370° C. and the outlet temperature was controlled at 190° C.

Subsequently, calcination was performed at 590° C. for 3 hours in a muffle furnace without a preliminary calcination to obtain catalyst C5.

The Mo/Si atomic ratio in the bulk composition of the catalyst C5 measured with ICP emission spectrometry was 0.29. This value substantially coincided with those values obtained with catalysts C3 and C4 in Example 2 and Example 3, respectively.

Further, the Mo/Si atomic ratio in surface composition of the particles of the catalyst C5 measured with X-ray Photoelectron Spectroscopy was 0.22.

That is, the ratio of the Mo/Si atomic ratio in surface composition of the catalyst particles to the Mo/Si atomic ratio in bulk composition of the catalyst in the catalyst C5 was 0.76.

The aforesaid activity test was performed with the catalyst C5 under the conditions that the contact time was 2.8 sec, and the conversion rate of propylene, selectivity to acrylonitrile and yield of acrylonitrile after 3 hours from the start of the reaction were 98.1%, 83.3% and 81.7%, respectively.

When the reaction was continued with the condition left intact, and the analysis was performed again after 500 hours from the start of the reaction, the conversion rate of propylene, selectivity to acrylonitrile and yield of acrylonitrile were 97.0%, 81.2% and 78.8%, respectively.

Comparative Example 3

Solution D and solution E were prepared in the same manner as in Example 2.

While solution D was being thoroughly stirred, solution E was mixed into it and the resulting solution was heated to 95° C. and aged at the same temperature for 3 hours to make a slurry.

The resulting slurry was spray dried using a pressure nozzle type spray dryer in which the inlet temperature of hot air was controlled at 310° C. and the outlet temperature was controlled at 230° C.

Subsequently, calcination was performed at 590° C. for 3 hours in a muffle furnace without a preliminary calcination to obtain catalyst C6.

The Mo/Si atomic ratio in the bulk composition of the catalyst C6 measured with ICP emission spectrometry was 0.29. This value substantially coincided with those values obtained with catalysts C3 and C4 in Example 2 and Example 3, respectively.

Further, the Mo/Si atomic ratio in surface composition of the particles of the catalyst C6 measured with X-ray Photoelectron Spectroscopy was 0.21.

That is, the ratio of the Mo/Si atomic ratio in surface composition of the catalyst particles to the Mo/Si atomic ratio in bulk composition of the catalyst in the catalyst C6 was 0.72.

The aforesaid activity test was performed with the catalyst C6 under the conditions that the contact time was 2.8 sec, and the conversion rate of propylene, selectivity to acrylonitrile and yield of acrylonitrile after 3 hours from the start of the reaction were 98.0%, 83.1% and 81.4%, respectively.

When the reaction was continued with the condition left intact, and the analysis was performed again after 500 hours from the start of the reaction, the conversion rate of propylene, selectivity to acrylonitrile and yield of acrylonitrile were 97.3%, 81.4% and 79.2%, respectively.

INDUSTRIAL APPLICABILITY

The present invention is a catalyst for acrylonitrile synthesis which comprises a particle containing silica and a composite oxide including at least molybdenum wherein the Mo/Si atomic ratio in bulk composition of the catalyst, expressed as A, and the Mo/Si atomic ratio in surface composition of the catalyst particles, expressed as B, have a relationship such that B/A is not greater than 0.6, and therefore, when using this catalyst in a reaction for synthesizing acrylonitrile by gas-phase catalytic ammoxidation of propylene with molecular oxygen and ammonia, the acrylonitrile yield, especially, acrylonitrile selectivity can be maintained at a high level for a long time.

The invention claimed is:

1. A catalyst comprising a particle comprising silica and a composite oxide comprising molybdenum,
    wherein the catalyst comprises a bulk composition and a surface composition,
    wherein the Mo/Si atomic ratio in the bulk composition of the catalyst, expressed as A, and the Mo/Si atomic ratio in the surface composition of the catalyst, expressed as B, have a relationship such that B/A is not greater than 0.45,
    wherein the bulk composition of the catalyst is expressed by the formula 1:

$$Sb_aMo_bC_cD_dE_eO_f(SiO_2)_g \qquad (1)$$

wherein, Sb, Mo, and O are antimony, molybdenum, and oxygen, respectively;
   wherein C is at least one element selected from the group consisting of iron, cobalt, nickel, manganese, uranium, cerium, tin and copper;
   wherein D is at least one element selected from the group consisting of vanadium and tungsten;
   wherein E is at least one element selected from the group consisting of magnesium, calcium strontium, barium, lanthanum, titanium, zirconium, niobium, tantalum, chromium, rhenium, ruthenium, osmium, rhodium, iridium, palladium, platinum, silver, zinc, cadmium, boron, aluminum, gallium indium, sodium, potassium, rubidium, cesium, thallium, germanium, lead, phosphorus, arsenic, bismuth, selenium, and tellurium;
   wherein $SiO_2$ is silica;
   wherein the subscripts a, b c, d, e, f and g each represent an atomic ratio of each element;
   wherein a is 10, b ranges from 0.1 to 15, c ranges from 1 to 20, d ranges from 0 to 10, e ranges from 0 to 20, g ranges from 10 to 200 and f is the atomic ratio of oxygen that fulfills the requirement of the valence of each element above.

2. The catalyst of claim 1, wherein B/A is not greater than 0.3.

3. A method for preparing a catalyst according to claim 1, comprising:
    preparing an aqueous slurry comprising molybdenum and silica;
    drying the aqueous slurry in a drying chamber of a spray dryer; and
    calcining the dried slurry;
    wherein hot air flows through the drying chamber, and the difference in the temperature of the hot air at an inlet of the drying chamber and the temperature of the hot air at an outlet of the drying chamber ranges from 20° C. to 60° C.

4. A catalyst comprising a particle comprising silica and a composite oxide comprising at least molybdenum,
    wherein the catalyst comprises a bulk composition and a surface composition,
    wherein the Mo/Si atomic ratio in the bulk composition of the catalyst, expressed as A, and the Mo/Si atomic ratio in the surface composition of the catalyst, expressed as B, have a relationship such that B/A is not greater than 0.45,
    wherein the bulk composition of the catalyst is expressed by the formula 2:

$$Mo_hBi_iFe_jF_kG_lO_m(SiO_2)_n \qquad (2)$$

wherein Mo, Bi, Fe and O are molybdenum, bismuth, iron, and oxygen, respectively;
   wherein F is at least one element selected from the group consisting of sodium, potassium, rubidium, cesium, and thallium;
   wherein G is at least one element selected from the group consisting of cobalt, nickel, copper, zinc, magnesium, calcium, strontium, barium, titanium, vanadium, chromium, manganese, tungsten, silver, aluminum, phosphorus, boron, tin, lead, gallium, germanium, arsenic, antimony, niobium, tantalum, zirconium, indium, sulfur, selenium, tellurium, lanthanum, cerium, praseodymium, neodymium, samarium, europium, gadolinium, terbium, holmium, erbium, thulium and ytterbium;
   wherein $SiO_2$ represents silica;
   wherein h, i, j, k, l, m and n each represents an atomic ratio of each element;
   when h is 12, i ranges from 0.1 to 5, j ranges from 0.1 to 10, k ranges from 0.01 to 3, l ranges from 0 to 20, n ranges from 10 to 200 and m is the atomic ratio of oxygen that fulfills the requirement of the valence of each element above.

5. The catalyst of claim 4, wherein B/A is not greater than 0.3.

6. A method for preparing a catalyst according to claim 4, comprising:
    preparing an aqueous slurry comprising molybdenum and silica;
    drying the aqueous slurry in a drying chamber of a spray dryer; and
    calcining the dried slurry;
    wherein hot air flows through the drying chamber, and the difference in the temperature of the hot air at an inlet of the drying chamber and the temperature of the hot air at an outlet of the drying chamber ranges from 20° C. to 60° C.

* * * * *